United States Patent
Osborne et al.

(10) Patent No.: US 6,432,415 B1
(45) Date of Patent: Aug. 13, 2002

(54) PHARMACEUTICAL GEL AND AEROSOL FORMULATIONS AND METHODS TO ADMINISTER THE SAME TO SKIN AND MUCOSAL SURFACES

(75) Inventors: David W. Osborne, Fort Collins, CO (US); Russell J. Mumper, Lexington, KY (US)

(73) Assignee: Axrix Laboratories, Inc., Fort Collins, CO (US)

( * ) Notice: Subject to any disclaimer, the term of this patent is extended or adjusted under 35 U.S.C. 154(b) by 0 days.

(21) Appl. No.: 09/466,380

(22) Filed: Dec. 17, 1999

(51) Int. Cl.$^7$ ................................................ A61K 7/00
(52) U.S. Cl. ...................................... 424/400; 424/401
(58) Field of Search ........................ 424/401, 45, 443, 424/400

(56) References Cited

U.S. PATENT DOCUMENTS

| | | |
|---|---|---|
| 3,996,934 A | 12/1976 | Zaffaroni |
| 4,226,848 A | 10/1980 | Nagai et al. |
| 4,250,163 A | 2/1981 | Nagai et al. |
| 4,286,592 A | 9/1981 | Chandrasekaran |
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |

(List continued on next page.)

FOREIGN PATENT DOCUMENTS

| | | |
|---|---|---|
| EP | 0 604 848 | 7/1994 |
| EP | 0 836 852 | 4/1998 |
| JP | 56-100714 | 8/1981 |
| WO | 98/17252 | 4/1998 |
| WO | WO 99/53913 | 10/1999 |

OTHER PUBLICATIONS

Ashworth et al. (1991). "Delivery of Propellant Soluble Drug From a Metered Dose Inhaler," *Thorax* 46:245–247.

Binnie et al. (1997). "Amlexanox Oral Paste: A Novel Treatment that Accelerates the Healing of Aphthous Ulcers," *Compend. Contin.. Educ. Dent.* 18(11):1116, 1118, 1120–1122, 1124, 1126.

Borum et al. (1996). "Comparison Between the Effect of Ipratropiurn Bromide as a Pressurized Aerosol and as an Aqueous Pump Spray on Methacholine–Induced Rhinorrhea," *Rhinology* 34:198–200.

Bundgaard et al. (1989). "Prodrugs of Peptides. IV: Bioreversible Derivatization of the Pyroglutamyl Group by N–Acylation and N–Aminomethylation to Effect Protection Against Pyroglutamyl Aminopeptidase," *J. Pharm. Sci.* 78(2):122–126.

(List continued on next page.)

*Primary Examiner*—Jose' G. Dees
*Assistant Examiner*—Konata M George
(74) *Attorney, Agent, or Firm*—Morrison & Foerster LLP (57) ABSTRACT

Bioadhesive formulations to deliver, for both local and systemic effects, a wide variety of drugs of varying degrees of solubility are described. These formulations can be gels or aerosols and comprise a water-insoluble, pharmaceutically acceptable alkyl cellulose, a solvent system comprising a volatile solvent and water, a solubilizing agent or a dispersing agent, or a mixture thereof, and a pharmaceutical. These formulations can be made bioerodible and release the pharmaceutical in a controlled manner. Formulations further comprising a propellant such as 1,1-difluoroethane are also provided. The delivery can be made to a skin surface or to a mucosal surface. Methods for preparing and administering these formulations are also provided. Several specific examples using the anti-ulcer medication 2-amino-7-(1-methylethyl)-5-oxo-5H-[1]benzopyrano-[2,3-b]-pyridine-3-carboxylic acid are provided.

43 Claims, 3 Drawing Sheets

Amlexanox Solubility in 95% ethanol is
Enhanced in the presence of Imidazole

U.S. PATENT DOCUMENTS

| | | | |
|---|---|---|---|
| 4,572,832 | A | 2/1986 | Kigasawa et al. |
| 4,713,243 | A | 12/1987 | Schiraldi et al. |
| 4,894,232 | A | 1/1990 | Reül et al. |
| 4,900,554 | A | 2/1990 | Yanagibashi et al. |
| 4,915,948 | A | 4/1990 | Gallopo et al. |
| 5,081,157 | A | 1/1992 | Pomerantz |
| 5,081,158 | A | 1/1992 | Pomerantz |
| 5,137,729 | A | 8/1992 | Kuroya et al. |
| 5,192,802 | A | 3/1993 | Rencher |
| 5,298,258 | A | 3/1994 | Akemi et al. |
| 5,314,915 | A | 5/1994 | Rencher |
| 5,362,737 | A | 11/1994 | Vora et al. |
| 5,642,749 | A | 7/1997 | Perryman |

OTHER PUBLICATIONS

Daubländer et al. (1992). "Clinical Investigation of Potency and Onset of Different Lidocaine Sprays for Topical Anesthesia in Dentistry," *Anesth. Pain Control Dent.* 1(1):25–28.

Gennaro ed. (1995). *Remington: Practice of the Science and Pharmacy.* Nineteenth Edition, Mack Publishing Co.: Easton, P.A., Ch. 16(pp. 194–212), Ch. 80(1380–1416), Ch. 83(1447–1462), Ch. 95(1676–1694).

Harris et al. (1988). "Effect of Viscosity on Particle Size, Deposition, and Clearance of Nasal Delivery Systems Containing Desmopressin," *J. Pharm. Sci.* 77(5):405–408.

Ibrahim et al. (1993). "Effect of Formulation pH and Storage Temperatures on the Preservative Efficacy of Some Gases Used as Propellants in Cosmetic Aerosols," *J. Appl. Bacteriol.* 74:200–209.

Martin et al. eds. (1983). *Physical Pharmacy: Physical-Chemical Principles in the Pharmaceutical Sciences.* Third Edition, Lea & Febiger: Philadelphia, pp. 66, 325–326, 544–553, 614–615.

*The United States Pharmacopeia: The National Formulary.* (Jan. 1, 1995). United States Pharmacopeial Convention, Inc.: Rockville, MD., 4 pages total (Table of Contents).

Figure 1. Amlexanox Solubility in 95% ethanol is Enhanced in the presence of Imidazole Figure 2. Amlexanox and Imidazole form a 1:1 mole Complex in 95% ethanol as demonstrated by the Continuous Variation Method Figure 3. HPLC Assay for the Detection and Quantification of Amlexanox

PHARMACEUTICAL GEL AND AEROSOL FORMULATIONS AND METHODS TO ADMINISTER THE SAME TO SKIN AND MUCOSAL SURFACES

FIELD OF THE INVENTION

The present invention relates to the general field of pharmaceutical arts. More specifically, the invention relates to pharmaceutical gel and aerosol formulations made from film-forming water-insoluble polymers.

BACKGROUND ART

Bioadhesive pharmaceutical formulations can be used to deliver drugs locally at the site of application or systemically through absorption from the site of application. In either type of intended delivery, one primary requirement is that an effective concentration of the particular pharmaceutical be maintained at the site of application for a sufficient period of time such that the pharmaceutical can act locally or be absorbed for systemic effects.

Given the tendency of natural bodily fluids to rapidly wash away topically applied pharmaceutical components, topical application to wet mucosal surfaces or other body tissues has been problematic. For example, in the mouth, saliva, natural replacement of the mucosal surface, and movements associated with eating, drinking, and speaking are some of the factors that have limited the effectiveness and residence time of pharmaceutical carriers.

Bioadhesive formulations are known in the art and include gels, pastes, tablets, and films. For example, U.S. Pat. Nos. 5,192,802, 5,314,915, 5,298,258, and 5,642,749 describe bioadhesive gels. Denture adhesive pastes are described in, for example, U.S. Pat. Nos. 4,894,232 and 4,518,721. A commercial product under the name Orabase®-B, which is a thick gel or paste for the relief of mouth sores, is another example of an adhesive paste. Bioadhesive tablets are described in U.S. Pat. Nos. 4,915, 948, 4,226,848, 4,292,299, and 4,250,163, as having single layer or bilayers. U.S. Pat. Nos. 3,996,934 and 4,286,592 describe the use of bandages or bioadhesive laminated films.

U.S. Pat. Nos. 4,517,173, 4,572,832, 4,713,243, 4,900, 554, and 5,137,729 describe delivery systems for use on mucosal surfaces. U.S. Pat. No. 4,381,296 describes a suspension of tannic acid, salicylic acid, and boric acid in ethanol wherein no gelling agent was used.

U.S. Pat. Nos. 5,081,157 and 5,081,158 describe compositions made of hydroxypropyl cellulose, a non-toxic volatile solvent, an esterification agent, and a medicinal component. A crosslinking agent may also be used. The '158 Patent teaches that alkyl or hydroxyalkyl substituted cellulose are not suitable substitutes for hydroxypropyl cellulose (column 2, lines 28–31) for forming films on body tissues.

Japanese Patent publication JP 56-100714 describes a preparation which comprises an uneven distribution of a medicinal layer in a coating layer by creating a tablet for mucosal adhesion. This preparation includes surfactants.

The above-described formulations appear to lack one or more preferred characteristics for an efficient and commercially acceptable bioadhesive pharmaceutical delivery device, namely, residence time at the site of application for a desired length; water-erodability; instantaneous adhesion upon application to the affected site such as mucosal surface; ease of handling and application to the affected site; ease of removal of the delivery device from the affected tissue or in a natural dissolution of the delivery device at the delivery site; and ease of comfort, with minimal foreign body sensation. Further, in all these cases, the ingredients comprising the formulation must be pharmaceutically acceptable.

More recently, pharmaceutical preparations made from film-forming water-insoluble polymers solubilized in pharmaceutically acceptable solvents, bioadhesive polymers, and at least one active pharmaceutical, and methods for their use have been described. See for example, PCT publication WO 9817252, published Apr. 30, 1998.

The above-described references, however, have not effectively addressed the issue of drug solubility in the formulation. Solubility influences a drug's dissolution, release kinetics, and ultimately its bioavailability and thus plays a major role in the preformulation stage of many pharmaceuticals. See generally, REMINGTON: THE SCIENCE AND PRACTICE OF PHARMACY, CHAPTER 83, MACK PUBL. CO., EASTON (19 TH EDITION, 1995) (hereinafter, REMINGTON). Since many pharmaceuticals are not very soluble in the formulation, the number of available dosage forms is limited for such pharmaceuticals. The present invention addresses this problem and provides pharmaceutical gels and aerosol formulations that are capable of delivering drugs of varying solubility characteristics.

DISCLOSURE OF THE INVENTION

The present invention provides non-water soluble, film-forming bioadhesive pharmaceutical formulations comprising:
  a water-insoluble alkyl cellulose from about 0.1% to about 20% by weight of the formulation;
  a solvent system comprising a mixture of from about 30% to about 90% by weight of at least one volatile solvent and up to about 25% by weight of water;
  a solubilization agent or a dispersing agent or a mixture thereof, and
  a pharmaceutical.

The alkyl cellulose may be methyl cellulose, ethyl cellulose, propyl cellulose, or butyl cellulose, or a mixture thereof and the volatile solvent may be a lower alkyl alcohol, 1-methyl-2-pyrrolidone, a volatile silicone, a propellant, or a mixture thereof. In some aspects, the pharmaceutical is not very soluble in the formulation in the absence of a solubilization agent. The solubilization agent may be imidazole.

The formulations may further comprise a liquified gas propellant or a compressed gas propellant or a mixture thereof. In some aspects, the propellant is 1,1-difluoroethane.

Additionally, non-water soluble, film-forming bioadhesive pharmaceutical formulations are provided comprising:
  ethylcellulose which constitutes from about 0.1% to about 20% by weight of the formulation;
  a solvent system comprising a mixture of at least one volatile solvent and up to about 25% by weight of water; and
  a pharmaceutical.

The volatile solvent may be a lower alkyl alcohol, 1-methyl-2-pyrrolidone, a volatile silicone, or a mixture thereof. In one aspect, the volatile solvent comprises ethanol.

Further, the formulations may comprise from about 1% to about 10% by weight of a polymer having bioadhesive properties, wherein said bioadhesive polymer is polycarbophil, polyacrylic acid, polyvinylpyrrolidone, sodium carboxymethyl cellulose, or a mixture thereof. In some aspects, the above formulations may further comprise an adjuvant.

The formulations may also comprise a bioerodable polymer, wherein the bioerodable polymer is hydroxypropyl cellulose or a copolymer of lactic and glycolic acids, polycaprolactone, a polyorthoester, polyphosphazene or a mixture thereof.

The formulations can be prepared such that the pharmaceutical is released in a controlled manner. In some aspects, the pH of the formulation is from about 4.0 to about 7.0.

The above formulations can be prepared in an aerosol form. In such cases, a liquified gas propellant or a compressed gas propellant or a mixture thereof can be used to deliver the formulation. In some aspects, the propellant is 1,1-difluoroethane. Alternatively, mechanical means (i.e., without a propellant) can also be used to deliver the formulation. In some aspects, water constitutes greater than about 5% by weight of the above formulations.

A broad category of drugs can be delivered using the formulations of the present invention. One specific but nonlimiting example is Amlexanox, 2-amino-7-(1-methylethyl)-5-oxo-5H-[1]benzopyrano-[2,3-b]-pyridine-3-carboxylic acid, which constitutes from about 0.5% to about 5% by weight of the formulation.

In one aspect, a non-water soluble, film-forming bioadhesive pharmaceutical formulation is provided comprising:
 ethylcellulose which constitutes from about 0.1% to about 20% by weight of the formulation;
 ethanol which constitutes from about 60% to about 90% by weight of the formulation;
 water up to about 25% by weight of the formulation;
 hydroxypropylcellulose as a bioerodable polymer constituting up to about 2% by weight of the formulation;
 polyvinylpyrrolidone, polycarbophil or a mixture thereof as a bioadhesive polymer constituting from about 1% to about 10% by weight of the formulation; imidazole constituting from about 0.01% to about 5% by weight of the formulation; and
 2-amino-7-(1-methylethyl)-5-oxo-5H-[1]benzopyrano-[2,3-b]-pyridine-3-carboxylic acid, which constitutes from about 0.5% to about 5% by weight of the formulation.

Methods for delivery of an effective amount of one or more pharmaceuticals to a skin surface or a mucosal surface are also provided. Such methods comprise administering one or more of the above-described formulations to the skin surface or to the mucosal surface.

MODES FOR CARRYING OUT THE INVENTION

A. General Techniques

One of ordinary skill in the art would readily appreciate that the pharmaceutical formulations described herein can be prepared by applying known pharmaceutical manufacturing procedures. Such formulations can be administered to the subject by using methods that are well-known in the pharmaceutical arts. Thus, the practice of the present invention will employ, unless otherwise indicated, conventional techniques of pharmaceutical sciences including pharmaceutical dosage form design, drug development, and pharmacology, as well as of organic chemistry, including polymer chemistry. Accordingly, these techniques are within the capabilities of one of ordinary skill in the art and are explained fully in the literature. See generally, for example, REMINGTON, supra.

B. Definitions

As used herein, certain terms may have the following defined meanings.

As used in the specification and claims, the singular form a, an and the include plural references unless the context clearly dictates otherwise. For example, the term a pharmaceutical may refer to one or more pharmaceuticals for use in the presently disclosed formulations and methods.

The term pharmaceutical includes any known pharmacologically active agent as well as its pharmaceutically acceptable salt, prodrug such as an ester or an ether, or a salt of a prodrug, or a solvate such as ethanolae, or other derivative of such pharmacologically active agent. These salts, prodrugs, salts of prodrugs, solvates and derivatives are well-known in the art.

Salts of the pharmacologically active agents may be derived from inorganic or organic acids and bases. Examples of inorganic acids include hydrochloric, hydrobromic, sulfuric, nitric, perchloric, and phosphoric acids. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of organic salts include: acetate, propionate, butyrate, hexanoate, heptanoate, undecanoate, palmoate, cyclopentanepropionate, adipate, alginate, aspartate, benzoate, citrate, oxalate, succinate, tartarate, lactate, maleate, fumarate, camphorate, nicotinate, pectinate, picrate, pivalate, tosylate, gluconate, digluconate, hemisulfate, methanesulfonate, ethanesulfonate, 2-hydroxyethanesulfonate, dodecylsulfate, camphorsulfonate, benzenesulfonate, 2-naphthalenesulfonate, thiocyanate, phosphate, glycerophosphate, and phenylpropionate. Several of the officially approved salts are listed in REMINGTON, supra, Chapter 83.

The term derivative of a compound as used herein means a chemically modified compound wherein the chemical modification takes place at one or more functional groups of the compound and/or on an aromatic ring, when present. The derivative however is expected to retain the pharmacological activity of the compound from which it is derived.

The term prodrug refers to a precursor of a pharmacologically active compound wherein the precursor itself may or may not be pharmacologically active but, upon administration, will be converted, either metabolically or otherwise, into the pharmacologically active drug of interest. Several prodrugs have been prepared and disclosed for a variety of pharmaceuticals. See, for example, Bundgaard, H. and Moss, J., *J Pharm. Sci.* 78: 122–126 (1989). Thus, one of ordinary skill in the art knows how to prepare these derivatives and prodrugs with commonly employed techniques of organic synthesis.

In addition, this invention contemplates the use of polymorphic, isomeric (including stereoisomeric, geometrically isomeric and optically isomeric) and anomeric forms of the pharmaceuticals described herein.

The terms pharmaceutical and drug as used herein are identical in meaning and thus are used interchangeably.

The term pharmaceutically acceptable means that the ingredient that is being qualified is compatible with the other ingredients of the formulation and not injurious to the patient. Several pharmaceutically acceptable ingredients are known in the art and official publications such as THE UNITED STATES PHARMACOEPIA describe the analytical criteria to assess the pharmaceutical acceptability of numerous ingredients of interest.

The term pharmaceutical carrier or simply carrier as used herein refers to a composition that contains and or delivers a pharmacologically active agent and is generally considered to be otherwise pharmacologically inactive. However, the carriers of this invention may have some therapeutic effect when applied to a site such as a mucous membrane or skin, by providing, for example, protection to the site of application from conditions such as injury, further injury, or exposure to elements. Thus, in some aspects, the carriers of this invention can be used for protection without a pharmacological agent in the formulation.

Formulation is a pharmaceutical term of art that includes a carrier and a pharmaceutical. As used herein, it specifically refers to non-solid dosage forms such as gels and aerosols.

A gel is defined as a semisolid consisting of large particles interpenetrated by a liquid. See PHYSICAL PHARMACY: PHYSICAL CHEMICAL PRINCIPLES IN THE PHARMACEUTICAL SCIENCES, A. Martin, J. Swarbrick, A. Cammarata, Eds., Lea & Febiger, Philadelphia (Third Edition, 1983) (hereinafter MARTIN'S PHYSICAL PHARMACY), at 614–615. Single-phase gels are comprised of polymers or some other large particles uniformly distributed throughout the liquid such that no discernable boundary exists between the polymers and the liquid. The polymer particles are referred to as the dispersed phase while the liquid (or the solvent system) is the continuous phase.

A solvent system is a mixture of at least one volatile solvent and water.

The term volatile refers to the characteristic of evaporating within a short time at ambient temperatures or at the temperature of a live human body. Thus a solvent is volatile if it evaporates at temperatures below 40° C. and within about ten to twenty minutes, preferably, within about five to ten minutes and more preferably, within about one to five minutes.

The terms gel solution and gel suspension are used to describe the physical state of the drug in the gel. In a gel solution, the drug is fully dissolved in the solvent system. In a gel suspension, the drug is mostly suspended in the solvent system, but a small portion of the drug may be still be dissolved.

Gel suspension stabilization agents are substances added to gel suspensions to keep the drug in suspension.

A solubilization agent increases the solubility of a pharmaceutical in the solvent system. The solubilization agent preferably comprises between about 0.01% and about 20% by weight of the final formulation, and more preferably between about 0.1% and 10% by weight of the final formulation.

A neutralizing agent, when added to a gel, causes conformational change to one or more of the components in the dispersed phase. The neutralizing agent preferably comprises between about 0.1% and about 20% by weight of the final formulation, and more preferably between about 0.1% and 10% by weight of the final formulation. Neutralizing agents can be either acids or bases. For example, for negatively charged polymers in the dispersed phase of the gel, a base added to the gel will neutralize the negative charge of the polymers which promotes uncoiling of the polymers. Polymer uncoiling results in a thickening of the gel.

Bases that can function as neutralizing agents are, but not limited to, the following: sodium hydroxide, potassium hydroxide, and low molecular weight amines.

A dispersing agent is an agent that facilitates the formation of a dispersion of one or more internal phases in a continuous phase. Examples of such dispersions include suspensions and emulsions, wherein the continuous phase may be water, for example, and the internal phase is a solid or a water-immiscible liquid, respectively. Thus, dispersing agents may include suspending agents and emulsifying agents.

An aerosol is a pharmaceutical term of art and as used herein refers generically to several types of aerosol formulations that are known in the art. See REMINGTON, supra, Chapter 95. Such aerosol formulations include propellant aerosols and mechanical pump spray aerosols.

A propellant is a substance that is a gas under atmospheric conditions but a liquid when under pressure. Pharmaceutically acceptable propellants are, but not limited to, the following: dimethyl ether; diethyl ether; fluorocarbons such as propellant 152a (1,1-difluoroethane, also known as Dymel®), a hydrocarbon, a liquified gas such as nitrogen or carbon dioxide or a mixture thereof.

A propellant aerosol is a formulation consisting of both a gel preparation and a pharmaceutically acceptable propellant under pressure. See MARTIN'S PHYSICAL PHARMACY, supra, at 66 for further descriptions of aerosols. For additional examples and applications of propellant aerosols, see also, Y. K. Ibrahim, and H. G. Sonntag, Effect of Formulation pH and Storage Temperatures on the Preservative Efficacy of Some Gases Used as Propellants in Cosmetic Aerosols. $J$ $Appl$ $Bacteriol$, 74(2):200–209 (1993); H. L. Ashworth, et al., Delivery of Propellant Soluble Drug from a Metered Dose Inhaler, $Thorax$, 46(4):245–247 (1991).

The propellant preferably comprises from about 15% to about 70% by weight of the final formulation, and more preferably from about 30% to about 60% by weight of the final formulation. When actuated, the pressure difference between the inside of the container and outside causes the rapid expansion of the propellant molecules and the ejection of the contents as a spray.

A pump spray is a formulation that does not contain a propellant and is ejected from a closed container by means of mechanical force (i.e., pushing down the accuator with one's finger). For examples and applications of pump sprays, see S. Borum, et al., Comparison Between the Effect of Ipratropium Bromide as a Pressurized Aerosol and as an Aqueous Pump Spray on Methacholine-induced Rhinorrhea, $Rhinology$ 34(4): 198–200 (1996); M. Daublander, et al., Clinical Investigation of Potency and Onset of Different Lidocaine Sprays for Topical Anesthesia in Dentistry, $Anesth.$ $Pain$ $Control$ $Dent.$, 1(1):25–28 (1992); and A. S. Harris, et al., Effect of Viscosity on Particle Size, Deposition, and Clearance of Nasal Delivery Systems Containing Desmopressin, $J$ $Pharm.$ $Sci.$, 77(5):405–408 (1988).

The term bio-erodable means that the component, carrier or formulation erodes, over time, in biological media such as bodily fluids and anatomical structures comprising or bathed by body fluids. Examples of bodily fluids include blood, plasma, saliva, tears, lymph, urine, etc. Examples of anatomical structures comprising or bathed by bodily fluids include the oral cavity, the nasal cavity, the genitourinary tract, the respiratory tract, the gastrointestinal tract, etc. Such erosion in bodily fluids may be due to factors such as dissolution, dispersion, friction, gravity, etc. Ther terms water-erodable and bioerodable are used interchangeably in this application.

The term kinetics of erodability or erosion kinetics refers to the timing of the release of pharmaceutical from the carrier or formulation (release profile), as well as, the timing of the erosion of the carrier or the formulation over time (lifespan or residence time of the carrier or formulation). Kinetics of erodability depend on factors such as and the nature of the carrier, the nature and amount of other ingredients such as the drug, additives or excipients in the formulation, the properties of the tissue to which the formulation is applied, the amount of formulation applied, the amount of saliva or other bodily fluid at the application site or surrounding areas, the contact surface, and other physiological factors. In a case in which a component of the carrier is very water soluble, the kinetics of erodability of the formulation will closely parallel the solubility kinetics of the carrier.

As used herein, the term solubility refers to the extent to which a solute dissolves in a solvent, wherein the solute and "solvent" may be of the same or of different physical state. Thus, a solution of a solid or a liquid in any "solvent" such as a solid, liquid or gas is within the scope of this term.

Solubility can be expressed in many ways, such as: weight/volume (grams/mL); molality (number of moles of solute/1000 grams of solvent); mol fraction (fraction of the total number of mols present which are mole of one component); mol % (mol fraction×100); normality (number of gram equivalent weights of solute dissolved in 1000 mL of solution); % by weight (% w/w); % weight in volume (% w/v); % by volume (% v/v).

Solubility can also be described by terms such as: very soluble (less than 1 part of solvent per 1 part of solute); freely soluble (from 1 to 10 parts of solvent per 1 part of solute); soluble (from 10 to 30 parts of solvent per 1 part of solute); sparingly soluble (from 30 to 100 parts of solvent for 1 part of solute); slightly soluble (from 100 to 1000 parts of solvent for 1 part of solute); very slightly soluble (from 1000 to 10,000 parts of solvent for 1 part of solute); and practically insoluble, or insoluble (more than 10,000 parts of solvent for 1 part of solute). For further elaboration, see REMINGTON, supra, Chapter 16, which is incorporated by reference.

An effective amount is an amount sufficient to effect beneficial or desired results. An effective amount can be administered in one or more administrations, applications or dosages. Determination of an effective amount for a given administration is well within the ordinary skill in the pharmaceutical arts.

The term administration refers to a method of delivering a formulation to a desired site. Several methods of administration are known in the art. Such methods include: applying, pressing, squeezing, spraying, dipping, rolling, rubbing, etc. Applying may include direct application by finger or a swab or other means of applying known in the art. Spraying may include the use of a propellant or mechanical means such as pump spraying.

Concentrations, amounts, etc., of various components of this invention are often presented in a range format throughout this application. The description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as 6% to 12% should be considered to have specifically disclosed subranges such as 6% to 7%, 7% to 8%, 7% to 9%, 6% to 9%, 9% to 12%, 9% to 11% etc., as well as individual numbers within that range, for example, 8%, 10%, 11% etc. This applies regardless of the breadth of the range and in all contexts throughout this application.

C. The Formulations

The present invention provides bioadhesive formulations to deliver drugs for both local and systemic effects. In some aspects, the formulation is a gel. In some aspects, the formulation is an aerosol. The drugs being delivered by these formulations can have a wide spectrum of solubility in the formulation, ranging from being freely soluble to insoluble.

The desired properties of the present invention are achieved in the combination of a water-insoluble alkyl cellulose, a solvent system, a solubilizing agent or a dispersing agent, and a pharmaceutical. The combination results in a non-water soluble gel which adheres to mucosal surfaces and skin surfaces. The non-water soluble bioadhesive gel can be further formulated into an aerosol, wherein the aerosol can be a pump spray type or propellant type. When the aerosol is of the propellant type, the formulation further comprises a pharmaceutically acceptable propellant.

(i) The Polymeric Gels

The water-insoluble alkyl cellulose polymers for use in this invention includes methyl cellulose, ethyl cellulose, propyl cellulose, butyl cellulose, or a mixture thereof In some aspects, the water-insoluble alkyl cellulose polymer is ethyl cellulose having the characteristics of an ethoxyl content from about 42% to about 52%, and more preferably from about 44% to about 50%, and a viscosity of between about 2 and about 500 cps, and more preferably between about 4 and about 400 cps as measured for about a 5% by weight of polymer in a 80/20 toluene/ethanol solution.

(ii) The Solvent System and Drug Solubility Aspects

The pharmaceutically acceptable solvent system for use in this invention comprises a mixture of a volatile solvent and water. Some examples of volatile solvents include lower alkyl alcohols, 1-methyl-2- pyrrolidone, volatile silicones or aerosol propellants. Examples of lower alkyl acohols include methanol, ethanol, isopropyl alcohol, ethoxydiglycol, etc. Examples of volatile silicones include polydimethylsiloxane, polyorganosiloxanes and other silicone polymers.

Aerosol propellants include: liquified gases and compressed gases. Liquified gases comprise hydrocarbons and hydrocarbon ethers, halocarbons, hydrohalocarbons such as hydrochlorofluorocarbons, hydrochlorocarbons. Examples of tiquified gases include 1,1-difluoroethane, 1,1,1,2-tetrafluoroethane, 1,1-difluoro-1,2,2-trichloroethane, propellants commonly known as A-108, A-13, A-17, A-24, A-70 etc, and dimethyl ether, and diethyl ether. Compressed gases include nitrogen, carbon dioxide and nitrous oxide. It is appreciated that the desirable solvent characteristics can also be obtained from a mixture of two or more of the above solvents.

The solvent system preferably comprises a mixture of about 40 to about 90 parts of a volatile solvent and up to 25 parts of water, and more preferably a mixture of about 55 to about 75 parts of a volatile solvent and up to about 15 parts of water. In one aspect, the solvent is a mixture of a volatile solvent such as ethanol, a propellant and water.

In one aspect, the propellant is 1,1-difluoroethane also known as Propellant 152a, commercially available under the trade mark Dymel®. Propellant 152a is slightly soluble in aqueous solvents (solubility of less than 1% by weight).

The present gel and aerosol formulations can be used to deliver drugs that have a wide spectrum of solubility characteristics. For example, the present gels and aerosols can be employed to deliver drugs characterized as "freely soluble," "soluble," "sparingly soluble," "slightly soluble," "very slightly soluble," "practically insoluble" or "insoluble."

Many pharmacologically active compounds are not very soluble in the solvents of the gel and aerosol formulations disclosed by the references described above in the Background section. For example, many drugs are not very soluble in solvents such as ethanol, isopropyl alcohol, ethoxydiglycol, and 1-methyl-2-pyrrolidone. Increasing the water content of the formulation may not be advisable because the increased water content may precipitate some of the dissolved polymers.

The present invention overcomes the solubility problem by enhancing drug solubility in the solvent system or by providing for a solution or dispersion of the drug in the solvent system, thereby providing novel formulations for these not-very-soluble drugs. As discussed above in the Background section, these formulations offer novel solutions to difficult preformulation problems of many pharmaceuticals.

The solubility of a charged drug can be improved by neutralizing the charge or shielding the charge by using pharmaceutically acceptable agents that have the opposite ionic charge as the drug. Neutralization or shielding of the charge on the drug may increase the solubility of the drug in the lipophilic solvent by essentially increasing the hydrophobicity of the drug. For negatively charged drugs, one may use pharmaceutically acceptable agents with a positive charge such as chitosan and its derivatives, calcium, imidazole, Eudragits®, gelatin, or pharmaceutically acceptable cationic surfactants. For positively charged drugs, one may use pharmaceutically acceptable agents with negative charge such as polyacrylic acid and its copolymers and derivatives, sodium carboxymethyl cellulose, alginates and their copolymers and derivatives, and negatively charged surfactants.

Agents that can form hydrogen-bonding with a drug include, but are not limited to, the following: polyvinylpyrrolidone and its copolymers, polyvinyl alcohol and its copolymers, blocked polymers of propylene oxide and ethylene oxide, such as Pluronic®, polysorbates such as Tweens®, polyethylene glycol and its copolymers and derivatives, polyacrylic acid and its copolymers and derivatives, and celluloses and their copolymers and derivatives.

Changes in ionic strength can be achieved by using pharmaceutically acceptable salts of sodium, calcium, magnesium, etc. Changes in pH can be achieved with pharmaceutically acceptable buffers such as citrate, phosphate, borate, acetate, carbonate, etc.

In one aspect, the formulation comprises a solubilization agent such as a base or acid, depending upon the characteristics of the drug that is being solubilized. In one further aspect, the solubilization agent is a base. In another aspect, the base is an inorganic base such as sodium hydroxide. In some aspects, the solubilization agent constitutes from about 1% to about 10% by weight of the formulation. In another aspect, the solubilization agent constitutes, preferably, from about 1% to about 6% and more preferably, from about 2% to about 5% by weight of the formulation.

In another aspect, the solubilization agent is imidazole. The formulation may contain imidazole from about 0.01% to about 5% by weight of the formulation. In some preferred aspects, the imidazole constitutes from about 0.1% to about 2% by weight of the formulation. Alternatively expressed, the concentration of imidazole may range from about 25 mM to about 200 mM. The appropriate amounts in a given case can be determined with relative ease by one of ordinary skill in the art in light of the present disclosure.

Stable drug dispersions are often difficult to accomplish due to physical issues relating to drug particle size and morphology, interfacial surface tension, settling, and particle aggregation (see *MARTIN'S PHYSICAL PHARMACY*, supra, at 544–553), requiring some times the addition of a dispersing agent.

The choice and amount of a dispersing agent may be influenced by several factors such as: a) hydrophile-lipophile balance (HLB) of the components in the formulation; b) ratio of organic solvent to water, c) particle size and total surface area of the drug particles, d) pharmaceutical acceptability of the dispersing agent, and e) solubility and HLB of the dispersing agent.

Potentially useful dispersing agents include, but are not limited to, the following: sorbitan esters such as monolaurate, monopalmitate, monostearate, trioleate, tristearate, polysorbate 20, polysorbate 40, polysorbate 60, and polysorbate 80; gums such as acacia, tragacanth, xanthan, guar, and veegum; colloids such as carrageenan, alginates, gelatin, agar and bentonite; copolymers and derivatives of: polyvinylpyrrolidone, polyvinyl alcohol, cellulose, polyethylene glycol, polyoxyethylene, poloxamers, carbomers, and chitosan. Other agents such as sodium lauryl sulfate, oleic acid and its salts and esters, N-acetyl-N-ethyl morpholinum ethosulfate, and glycerol monstearate are also useful. Use of these dispersing agents may result in suspensions or emulsions.

It is appreciated that a drug dispersion in the gel formulation may, in fact, constitute a sustained release delivery system for the drug. For example, when applied to mucosal surfaces or the skin, the gel formulation containing drug in suspension will form a strong film with solid drug particles dispersed throughout the film. Due to the influx of body fluids, the drug particles will slowly be wetted. This wetting process, and subsequent erosion of the particles, will serve to release solubilized drug in a controlled manner.

It is also appreciated that at any given time, some of the drug may be dissolved in the formulation while the undissolved drug may be dispersed in the formulation. Thus, a "pure" solution or a "pure" dispersion may or may not exist in the formulation. One of ordinary skill in the art will recognize that so long as the drug is in solution or uniformly dispersed throughout the formulation such that the drug release profile is not affected, the objectives of the present invention can be achieved.

In the case of aerosol formulations that use a propellant, typically, the aerosol propellants are not that freely miscible with water further aggravating the solubility problem. This has been especially noted in the context of one of propellants within the scope of this invention, namely, Propellant 152a. To improve its miscibility with water, a co-solvent such as ethanol, 2-propanol, dimethyl ether or acetone must be used in order to produce a clear solution. However, in the case of preparing a pharmaceutically acceptable aerosol formulation, the choice of cosolvent is extremely limited, and in many cases, to the use of ethyl alcohol. The alternative is to form an emulsion, which may not be desirable in many cases where a homogenous solvent system is much preferred over dispersions. See, *REMINGTON*, supra, Chapter 95, page 1682, left column.

The inventors have experimented with ethanol as a cosolvent to be used in conjunction with Propellant 152a. When water is added to the ethanol/Propellant 152a mixture, the solubility of Propellant 152a decreases. For example, Propellant 152a has a solubility of about 49% in a mixture of ethanol/water (80:20). However, the inventors have discovered that when ethyl cellulose, from about 0.75% to about 10%, was added to ethanol or ethanol/water mixtures, the solubility of Propellant 152a increased unexpectedly to about 62 to 64%. For example, ethyl cellulose from about 0.7% to about 1.4% increased the solubility of Propellant 152a in a solvent system comprising ethanol/water (80:20) to about 62–64%. This unexpected increase in solubility was not observed when hydroxyethyl cellulose or hydroxypropyl cellulose was used instead of ethyl cellulose.

This unexpected increase in solubility of Propellant 152a is particularly advantageous for aerosol formulations comprising Propellant 152a because this reduces the need for using high amounts of ethanol to dissolve the Propellant. Such high amounts of ethanol may precipitate certain drugs such as proteins or peptides, among others. Further, the high amount of ethanol in an aerosol formulation tends to lower the head pressure needed in the aerosol container. Such reduction in head pressure may decrease the amount of total drug that can be delivered per container because as the usage of a multiple dose aerosol container progresses, the head pressure in the container decreases in general. As the head pressure decreases, the amount of the formulation expelled per actuation may change, leading to a substantial variation in dosage per actuation.

Thus, the use of ethyl cellulose to solubilize the Propellant 152a reduces the amount of ethanol needed to dissolve the Propellant and makes the formulation useful to deliver the formulation to a greater extent per container than otherwise, while improving the uniformity of amount of drug delivered per dose. Further, the use of ethyl cellulose facilitates the delivery of certain drugs which may require or benefit from a lower ethanol concentration in the formulation.

Another important aspect of this beneficial effect of ethyl cellulose is that it facilitates the use of greater amounts of water in the formulation. For example, water in an amount greater than 5% by weight is desirable from a formulation point of view. Increased water content in the formulation prevents certain drugs such as hormones or peptides from denaturing and losing their pharmacological activity. Increased water content also helps by increasing the solubility of certain not very water soluble drugs, thereby preventing their precipitation in the formulation.

From a practical pont-of-view, increased water content is desirable for the following reasons. When a subject administers a formulation to skin or mucosal surfaces, it is desirable that the formulation is not dehydrating and preferably moisturizing to prevent not only topical reactions to the formulations but also to keep the formulation adhering to the application site. Formulations containing nonaqueous solvents such as ethanol may give rise to this problem because ethanol is a dehydrating agent. The present discovery enables the development of formulations that have greater than 5% water content, preferably, greater than 10% and in some aspects, greater than 20% and even up to 30% water content by weight.

One of ordinary skill in the art may appreciate that ethyl cellulose may provide the above-described benefits to any formulation that employs a solvent that requires ethanol or other nonaqueous solvents of similar polarity and solubility characteristics. For example, ethyl cellulose may be employed to benefit a formulation comprising a variety of aerosol propellants such as hydrofluorocarbons, hydrochlorocarbons, or hydrocarbons and the use of a nonaqueous solvents such as ethanol, propanol, isopropanol, acetone, etc., in the formulation may be reduced. It is also appreciated that the formulations thus to be benefited from the use of ethyl cellulose are not limited to aerosol formulations but may comprise a variety of dosage forms such as solutions, suspensions, emulsions, gels, foams, films, etc.

Accordingly, in some aspects, the present formulations comprise ethyl cellulose from about 0.1% to about 20%, preferably from about 0.1% to about 10% by weight of the formulation. In some aspects, the ethyl cellulose may comprise from about 0.1% to about 2% by weight of the formulation.

(iii) The Pharmaceuticals

The formulations of the present invention can be used to deliver practically any drug. Accordingly, a wide variety of drugs encompassing a broad spectrum of pharmacological agents are contemplated as candidates for both local and or systemic delivery. The choice of a particular pharmaceutical depends merely on the treatment or application desired. Several examples of these pharmaceuticals are well-known in the art. For a comprehensive description of these pharmaceuticals, see *REMINGTON*, supra.

Some non-limiting examples of pharmacological classes of drugs that can be used in the present formulations include: analgesics, anti-inflammatory agents, both of steroidal and non-steroidal nature, antihistamines, antipruritics, general and local anesthetics, vasoconstrictors, antihypertensives including vasodilators, diuretics and ACE inhibitors, cardiac agents, hemostatics and styptics, mucolytics, antitussives, expectorants, mucoprotectants, antineoplastics, immunologic agents, antibiotics, antivirals, antidiabetics, bronchodilators, sympathomimetics, adrenergics, adrenergic blockers, anticholinergics, antimuscarinics, antispasmodics, skeletal muscle relaxants, uterine and antimigraine drugs, sedatives, hypnotics, anxiolytics, central nervous system stimulants, antidepressants and other psychopharmaceutical agents, antiepileptics, antiemetics and hormones.

While many of the above drugs have systemic and local effects, a number of pharmaceuticals of dermatological interest can be delivered to a skin surface for local effects by using the present formulations. Examples of some categories of such drugs include: topical antifungals, local anesthetics, topical bactericides and disinfectants, protectives and adsorbents, demulcents, emollients, astringents, antiperspirants, irritants, rubifacients, vesicants, keratolytics, cauterizing agents, cleansing agents, antiphlogistics, antipruritics, sunscreens, melanizers, skin bleaches, depilatories, hair growth enhancers such as minoxidil, vulnerary and epithelizing agents.

An exhaustive listing of specific examples of drugs for each of the above categories is not practical here, but many specific examples of these agents are provided in standard text books such as *REMINGTON*, supra and are well-known to one of ordinary skill in the art. To merely illustrate the breadth of possible agents that can be used, the following examples are provided.

Analgesics include opiate and non-opiate analgesics and antagonists of both synthetic and natural origin. Some examples are: morphine derivatives, codeine dervatives, methadone, propoxyphene, meperidine, fentanyl, morphinans such as levorphanol, and pentazocine. Other analgesics include acetaminophen.

Some examples of non-steroidal anti-inflammatory agents include: propionic acids such as fenoprofen, ibuprofen, ketoprofen; fenamates such as meclofenamate and mefenamic acid; acetic acids such as diclofenac, etodolac, indomethacin, sulindac; oxicams such as piroxicam; and other agents such as nabumetone. and oxyphenbutazone. Additionally, the following agents are also known as analgesic/anti-inflammatory agents: salicylates such as aspirin, methyl salicylate; monoglycol salicylate; salsalate; gold compounds such as auranofin; allopurinol, colchicine, and methysergide.

Examples of steroidal anti-inflammatory agents include hydrocortisone, prednisolone, dexamethasone, triamcinolone, fluocinolone, methylprednisolone, betamethasone, flumetasone, fluorometholone, beclomethasone, fluocinonide, etc.

Antihistamines can be of $H_1$ or $H_2$ antagonists or other types of histamine release inhibitors. The $H_1$ antagonists can be sedating or non-sedating. Examples of $H_1$-sedating antihistamines include diphenhydramine, chlorpheniramine, tripelennamine, promethazine, clemastine, doxylamine, etc. Examples of $H_1$-non-sedating antihistamines include astemizole, terfenadine, loratadine etc. Examples of $H_2$ antagonists include cimetadine, famotidine, nizatidine, and ranitidine. Examples of histamine-release-inhibitors include cromolyn.

Examples of local anesthetics include dibucaine, lidocaine, benzocaine, p-butylaminobenzoic acid -2-(diethylamino) ethyl ester, procaine, tetracaine, chloroprocaine, oxyprocaine, mepivacaine, bupivacaine, cocaine, piperocaine, dyclonine, etc.

Examples of vasoconstrictors include naphazoline, tetrahydrozoline, oxymetazoline, phenylephrine, etc.

Examples of hemostatics and styptics include thrombin, phytonadione, protamine, aminocaproic acid, tranexamic acid, rutin, hesperidin, silver salts, and ferric salts, etc.

Examples of antibacterials include sulfa drugs, penicillins, cephalosporins, tetracyclines, erythromycins, aminoglycosides, polypeptide antibiotics, fluoroquinolones, chloramphenicol, clindamycin, rifampin, spectinomycin, vancomycin, bacitracin, cyclosporine, dapsone, ethambutol, ethionamide, isoniazid,nitrofurantoin, pyrazinamide, and trimethoprim. Additional agents include antimalarials, amebicides, antiprotozoals, anthelmintics, pediculicides and scabicides.

Examples of antiviral drugs include viral DNA polymerase inhibitors such as foscarnet, protease inhibitors, thymidine kinase inhibitors, sugar or glycoprotein synthesis inhibitors, structural protein synthesis inhibitors, attachment and adsorption inhibitors, amantadine, and nucleoside analogues such as acyclovir, didanosine, ganciclovir, idoxuridine, ribavarin, trifluridine, vidarabine, zalcitabine, zidovudine, etc. acyclovir, penciclovir, valacyclovir, and ganciclovir.

Examples of mucolytics include potassium iodide, sodium thiocyanate, urea, guanidine hydrochloride, N-acetylcysteine, dithiotheritol, and proteolytic enzymes such as chymotrypsin and trypsin. These agents can be used to affect mucus production and the elasticity and viscosity of the mucus produced.

Examples of hormones include insulin, LHRH, growth hormone, calcitonin, thyroid hormones, and male and female hormones such as testosterones, estrogens and progesterones.

Examples of astringents include aluminum salts such as alum, aluminum acetate, aluminum chloride, aluminum chlorohydrates, aluminum sulfate, aluminum zirconium chlorohydrate, bismuth subcarbonate, bismuth subnitrate, calamine, glutaral, methenamine, potassium permanganate, resorcinol, silver nitrate, tannic acid, zinc caprylate, zinc chloride, zinc oxide, zinc pyrithione, zinc sulfate and zinc undecylenate.

Some examples of irritants, rubifacients, and vesicants include: anthralin, benzoin tincture, camphor, cantharidin, capsicum, coal tar, ichthammol, juniper tar, menthol, balsams such as Peruvian balsam and Tolu balsam.

Topical antifungals include haloprogin, ciclopirox, flucytosine, miconazole, econazole, clotrimazole, fluconazole, oxiconazole, sulconazole, metronidazole, itraconazole, ketoconazole, butaconazole, terconazole, nystatin, povidone-iodine, tolnaftate, benzoic acid, salicylic acid, mercuric oxide, resorcinol, triacetin, undecylenic acid and its calcium, copper and zinc salts.

Topical anesthetics include the local anesthetics described above and benzyl alcohol, camphor, camphorated metacresol, juniper tar, menthol, phenol, phenolate sodium, resorcinol, methyl salicylate, turpentine oil, camphor, menthol, methyl nicotinate, capasaicin, capsicum containing capsaicin, capsicum oleoresin containing capsaicin.

Examples of keratolytics and cauterizing agents include salicylic acid, podophyllum resin, podolifox, cantharidin, the chloroacetic acids and silver nitrate.

Examples of topical bactericides and disinfectants include thimerosal, phenol, thymol, benzalkonium chloride, benzethonium chloride, chlorhexidine, povidone iodine, cetylpyridinium chloride, eugenol, trimethylammonium bromide, etc.

In addition, the present gel and aerosol formulations can be used to deliver diagnostic agents and vitamins for topical as well as systemic use. The formulations can also be used to deliver macromolecules such as nucleic acids, polysaccharides, peptides and proteins.

(iv) The Delivery Site

The bioadhesive formulations described herein can effectively deliver drugs to a skin surface or a mucosal surface. Mucosal surfaces line several organs and anatomical areas of the human body. Organs and anatomical areas having mucosal surfaces include, for example, the oral cavity (e.g., mouth, buccal area, gingival area, tongue, throat, and pharynx), the respiratory tract (e.g., nose, trachea, bronchi, bronchioles), the gastrointestinal tract (e.g., stomach, esophagus, duodenum, small intestines), the genitourinary tract (e.g., uterus, cervix, vagina, ureter, bladder), and the rectum.

Thus, the scope of applicability of the presently disclosed formulations is quite broad. Any number of locally and systemically effective drugs can be delivered to the mucosal surfaces that are present in the above-described organs and anatomical parts. To illustrate, various pharmacological classes of drugs, from astringents to antibiotics can be delivered for local effects in the oral cavity, from anxiolytics to cardiovascular drugs can be delivered to mucosal surfaces in the oral cavity for absorption and systemic effects. Expectorants that break up the mucus in the throat can also be delivered for local effects.

Decongestants and antihistamines can be delivered to the respiratory tract for local effects (e.g., in the nose), whereas mucolytics can be delivered into the lungs to break up mucus and help those afflicted with altered mucus characteristics, such as those suffering from cystic fibrosis.

In some aspects, delivery to the mucosal surfaces of the gastrointestinal tract may include mucoprotective pharmaceuticals that help to heal an ulcerative or inflammatory condition. Some examples of mucoprotectants include misoprostil and sucralfate.

The formulations disclosed herein can advantageously deliver drugs to mucosal surfaces of the genitourinary tract. Such drugs can be used to alter the characteristics of the mucus in the genitourinary tract, namely, pH, viscosity, as well as to alter the bacterial and fungal flora and hormonal balance locally. Thus, hormonal drugs such as progesterones, estrogens, or their combinations, as well as vaginal antifungals, antibiotics, and pH altering agents can be delivered. Many specific pharmaceuticals belonging to these categories are well-known in the art.

Similarly, various locally and systemically effective drugs can be delivered to rectal mucosal surfaces. Local delivery may include to treat, for example, hemorrhoids, inflammatory conditions or infections. Systemic delivery via rectal mucosa may include antimigraine drugs such as ergotamines, antihistamines such as promethazine, and antiemetics such as trimethobenzamide. In those cases where rectal mucosal delivery is contemplated, the present formulations can be superior to traditional formulations such as suppositories or foams, because the present formulations offer better control over erosion kinetics, ease of use and less foreign body sensation.

(v) Additional Aspects

To the formulations described above, one or more polymers known for their bioadhesive properties may also be added. These bioadhesive polymers help control residence time of the formulation at the application site by strengthening the adhesive nature of the film, when adhesion has to be particularly effective for reasons relating to the nature of a particular drug, the specific site of application, or the duration of drug delivery. Residence times which may be achieved with this invention range from several minutes to a day or more, and preferably 15 minutes to several hours.

Some examples of bioadhesive polymers include, polycarbophil, polyacrylic acid, polyvinylpyrrolidone, sodium carboxymethyl cellulose, or a mixture thereof. The bioadhesive polymer may constitute from about 0.1% and about 10% by weight of the formulation, more preferably from about 1% and about 8% by weight of the formulation.

In another aspect, the formulations can be made bioerodible by selecting one or more appropriate bioerodible polymers. These polymers are advantageously eroded away in the presence of aqueous media such as biological fluids, membranes or mucosal surfaces. Accordingly, the residence time (i.e., the kinetics of erodability) of the formulation can be adjusted by selecting the appropriate polymer and its amount in the whole formulation to suit a desired application. Such bioerodible polymers include copolymers of lactic and glycolic acids, polycaprolactone, polyorthoesters, polyphosphazene and derivatives and mixtures thereof. The bioerodable polymer may constitute from about 0.1% to about 10%, preferably from about 1% to about 8% by weight of the total formulation.

Alternatively, hydroxypropyl cellulose can be used to provide bioerodability to the present formulations. In some aspects, the hydroxypropyl cellulose containing formulation may not need an esterification agent. When used, the hydroxypropyl cellulose may constitute from about 0.1% to about 10%, preferably, from about 0.1% to about 5%, and more preferably, from about 0.1% to about 2% by weight of the formulation. Advantageously, the bioerodability of the film formed from the formulation may be modified depending upon the. ratio of hydroxypropyl cellulose to the water-insoluble alkylcellulose.

The ratio of hydroxypropyl cellulose to water-inslouble alkylcellulose that is necessary to form a bioerodible film-forming gel may vary based on the other components. As the ratio of hydroxypropyl cellulose to the water-insoluble alkylcellulose increases, the water erodability increases, i.e., the films are more readily washed away. In one aspect, the ratio of hydroxypropyl cellulose to water-inslouble alkylcellulose is from about 32:1 to about 1:4.

In a further aspect, the pH of the formulation is maintained from about 4.0 to about 7.0, preferably from about 4.0 to about 6.0. When the pH of the formulation is maintained within these ranges, the formulation may have optimal bioadhesiveness. However, the formulation may be bioadhesive even when the pH is outside the range of 4.0 to 7.0.

In addition, a variety of pharmaceutical adjuvants can be added to these formulations to obtain desirable characteristics such as permeation enhancement at the site of application, increased mechanical strength of the polymer, aesthetic appearance, and consistency of the formulation. Permeation enhancers for use in this invention include sodium lauryl sulfate, sodium glycocholate, azone, EDTA, sodium cholate, sodium 5-methoxysalicylate, and others known in the art. Cross linking agents or plasticizers to modify the polymer's characteristics such as mechanical strength and stability may include esters such as dibutyl or diethyl phthalate, amides such as diethyldiphenyl urea, vegetable oils, fatty acids uch as oleic acid and myristyl acid.

Adjuvants to improve aesthetic appearance and consistency may include, for example, antioxidants, preservatives, coloring, flavoring and diluting agents, emulsifying agents, coating agents, excipients, thickeners, filtering agents, stabilizers (such as emulsion, or temperature stabilizers), aroma enhancers (perfumes), lubricants, dessicants, moisturizers and humectants such as glycerin, and viscosity controlling agents. Several specific examples of these agents have been described, inter alia, in *REMINGTON*, supra. See in particular, Chapter 80. These adjuvants may constitute from about 0.1% to about 3% by weight, more preferably from about 0.5% to about 2.5% by weight of the formulation.

D. Methods of Making

The present formulations may be prepared by various methods known in the art so long as the formulation is substantially homogenous, i.e., the pharmaceutical is distributed substantially uniformly within the formulation. Such uniform distribution facilitates control over drug release from the formulation.

To make the gel of the present invention, the various components are dissolved in the chosen solvent. Because of the possibility that one or more of the components might not be in solution, a dispersion may also be formed. The gelling step may take place at any moment and may be induced by, for example, the addition of a special component, a change in pH, a change in temperature, or over time.

For an aerosol spray, the formulation may be a solution in the container and the formulation gels upon dispensing. As one skilled in the art will appreciate, if an aerosol propellant is employed, suitable pressures, percentages, and containers are required. Specific details of making the present formulations are provided in the Examples below.

It is appreciated that the characteristics of the film, namely, residence time, thickness, tensile strength, release kinetics and erosion kinetics, may be varied greatly by controlling the components used to make the formulation and their relative percentages as well as by the addition of plasticizers, the use of cross linking agents, or the amount of solvent residual. Other factors of importance include the total amount of pharmaceutical incorporated into the formulation, the particular application site, and the physical and chemical characteristics of the particular drug or combination of drugs.

In view of the various factors to be considered in preparing a formulation for a given application, the relative percentages of the components of the present invention may vary. Preferably, the film forming polymers constitute from about 2% to about 20%, and more preferably from about 4% to about 14% by weight of the formulation. The volatile solvent may constitute preferably from about 30% to about 95% by weight of the formulation. More preferably, the solvent constitutes from about 40% to about 90% by weight of the formulation. The pharmaceuticals may constitute preferably from about 0.1% to about 25%, more preferably from about 0.2% to about 10% by weight of the formulation.

E. Methods of Administration

Methods for administering a pharmaceutical to a skin surface or a mucosal surface comprise administering the formulations of the present invention to the skin surface or the mucosal surface. Such administration may include applying, spraying, dipping, pressing, squeezing, rolling, rubbing, etc. Applying may include direct application by finger or swab, or other device. Spraying may include the use of a propellant or mechanical means such as pump spraying. Many techniques of administration are well-known in the art.

Upon application and adherence to the mucosal surface or skin, the volatile solvent evaporates, diffuses, or penetrates the surrounding tissues, and a film is formed. The film provides effective drug delivery locally to the application site, surrounding body tissues, and bodily fluids, while also providing protection to the application site. Since many drugs can be absorbed through the mucosal surface or the skin into the blood stream, in some cases rapidly, the formulations presented herein can be used to deliver drugs for faster systemic onset.

Thus, unlike the bioadhesive tablets which are known in the art, the gels and aerosols of the present invention offer controlled release kinetics that may include immediate release. Such immediate release may not be feasible in case of tablet formulations because of the necessary dissolution step. Further, in contrast to the bioadhesive tablets, the formulations of the present invention offer a very limited and almost nonexistent foreign body sensation.

The formulations and methods of this invention can also be combined with other suitable compositions and therapies.

F. Preferred Embodiments

To illustrate the many aspects of the present invention, it is provided herein several Examples of formulations which comprise a specific not-very-soluble drug known as Amlexanox or 2-amino-7-(1-methylethyl)-5-oxo-5H-[1]benzopyrano-[2,3-b]-pyridine-3-carboxylic acid. Amlexanox is not very soluble in lower alkyl alcohols (0.58 mg/mL, in dehydrated ethanol) or water (0.005 mg/mL). However, solubility of Amlexanox increases with pH. For example, the solubility of Amlexanox at pH 3.0, 5.96, and 8.03 is 0.012 mg/mL, 15.3 mg/mL, and 3590 mg/mL, respectively. Thus, at any given time, Amlexanox may be present in the formulation as a solution or suspension or both.

Amlexanox is the active ingredient in a commercial product that helps to accelerate the healing time of aphthous ulcers in the mouth. See W. H. Binnie, et al., Amlexanox Oral Paste: A Novel Treatment that Accelerates the Healing of Aphthous Ulcers. *Compend Contin. Educ. Dent.*:18(11): 1116–1118, 1120–1122 (1997). The exact mechanism of action of Amlexanox is not known but Amlexanox has been shown to possess antiinflammatory activity by inhibiting, inter alia, the formation of leukotrienes in vitro and the release of inflammatory mediators from mast cells. The currently available commercial formulation for Amlexanox is a 5% paste wherein the Amlexanox is not solubilized but dispersed. See U.S. Pat. No. 5,362,737. The paste formulation has a very short residence time in contact with the aphthous ulcer since the paste easily washes away in the mouth.

Amlexanox may also be used for the treatment of dermatitis, wound healing, and mucositis. In these cases, Amlexanox formulation must be applied to cover a greater skin or mucosal surface area than in the treatment of aphthous ulcers in the mouth. Accordingly, the present invention provides Amlexanox formulations in a propellant aerosol or pump spray. As described above, the propellant formulations comprise, in some aspects, a propellant such as 1,1-difluoroethane, ethanol, water and ethyl cellulose.

G. Examples

The following specific Examples are provided to illustrate further the multi-faceted nature of the invention. Accordingly, the following Examples should not be construed as limiting the scope of the invention.

The ingredients used in the following Examples were obtained from commercial sources as follows. Ethyl cellulose grades N-100 and N-50 and Hydroxypropyl cellulose HF were purchased from Hercules Aqualon, Wilmington, Del. Polyvinylpyrrolidone K-90 was purchased from BASF Corp., Parsippany, N.J. Polycarbophil Noveon AA1 was purchased from BF Goodrich, Inc., Cleveland, Ohio. Amlexanox was purchased from Access Pharmaceuticals, Dallas, Tex. Propellant 152a and Propellant A31 were purchased from E.I. du Pont de Nemurs, West Virginia. The sources of additional materials and equipment are indicated in the following Examples.

EXAMPLE 1

Three ethanol-based gel formulations were prepared (Gel A, Gel B, and Gel C) using the following components (by weight): 95% ethanol, ethyl cellulose N-100 4%, ethyl cellulose N-50 4%, hydroxypropyl cellulose HF 1.1%, sweet peppermint oil 4%, and polyvinylpyrrolidone K-90 (PVP). The % ethanol and PVP in the formulations were as follows: 85.1% and 2%, respectively for Gel A, 81.8% and 5%, respectively for Gel B, and 78.9% and 8%, respectively for Gel C. For Gels A–C, PVP served as the bioadhesive polymer. The purpose of varying the PVP concentration from 2% to 8% was to assess the in-vitro adhesive differences between formulations with different PVP concentrations. The viscosity (n=3) of Gel A, Gel B, and Gel C was 2017±50 cp, 2572±54 cp, and 4751±47 cP, respectively. The differences in viscosity were directly relate to the final PVP concentrations.

An in-vitro film erosion study was completed by first depositing 0.3 mL of each gel onto a glass microscope cover slide in triplicate and allowing the films to dry overnight at room temperature. When dry one cover slip from each group was suspended on the top of a beaker containing 200 mL of double-distilled water at room temperature. The cover slips with dried film were fully submerged in the water. The water was stirred using a magnetic stirrer at 75 rpm which was slow enough to avoid the formation of a vortex. Within 2 hours and 15 minutes, all films detached from the cover slide intact and remained intact even after stirring overnight. Although there appeared to be no difference between Gels A–C containing different concentrations of PVP, the films strongly adhered to negatively charged cover slips demonstrating adhesive properties.

EXAMPLE 2

Figure 1:
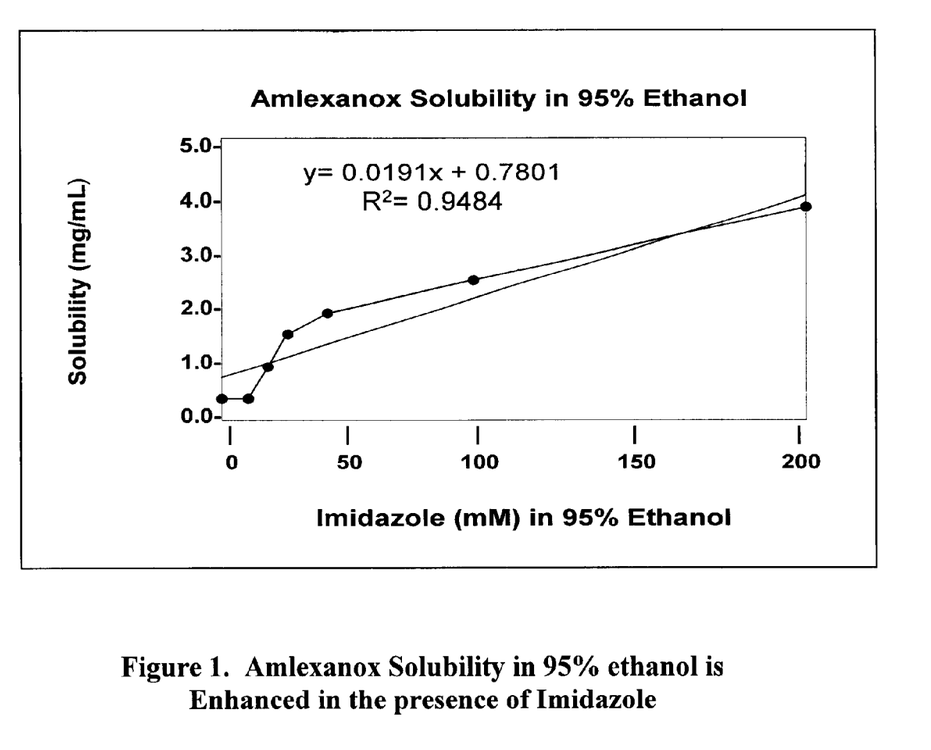
FIG. 1 is a graphical display of solubility of Amlexanox in 95% ethanol in the presence of imidazole, a solubilizing agent. This graph illustrates that imidazole enhances the solubility of Amlexanox in 95% ethanol.

Amlexanox (4.8 mg to 20.5 mg) was added to seven glass scintillation vials. 95% Ethanol (in 5–100 uL aliquots) with various concentrations of imidazole (0–200 mM) was added to the vials containing Amlexanox. The total volume of 95% ethanol added to result in Amlexanox solubilization (by visual observation) was recorded. The results are displayed in FIG. 1. As FIG. 1 shows, a direct relationship was found between the concentration of imidazole in 95% ethanol and the resulting solubility of Amlexanox. The solubility of Amlexanox in 95% ethanol with 200 mM imidazole was approximately 7.5-fold greater than the solubility of Amlexanox in 95% ethanol in the absence of imidazole. These results demonstrate that imidazole could function as a solubilization agent for Amlexanox and suggest that ethanol based gels could incorporate not very soluble drugs such as Amlexanox with imidazole as a solubilization agent.

The exact mechanism of increased solubilization is not clear but, without wishing to be bound to any particular theory or mechanism, it may be stated that such increased solubility may be due to hydrogen-bonding or charge interaction. If the increased solubilization was due to charge interaction one would expect a 1:1 mole ratio between imidazole and Amlexanox since each molecule contains one opposite charge. Job's Continuous Variation method (see MARTIN'S PHYSICAL PHARMACY, at 325–26) was utilized to ascertain the binding between imidazole and Amlexanox in 95% ethanol. These results are shown in FIG. 2.

Figure 2:
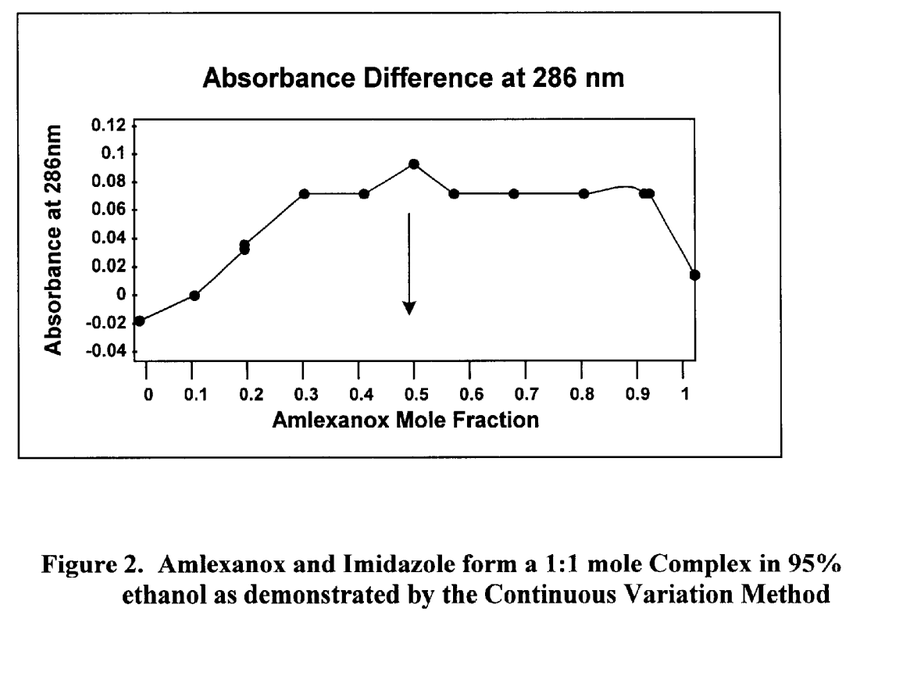
FIG. 2 is a graphical display of UV absorbance data of Amlexanox as measured by Continuous Variation Method. The graph illustrates that Amlexanox and imidazole appear to form an equimolar complex, which complex formation may explain the increased solubility of Amlexanox in 95% ethanol.

As FIG. 2 shows, UV absorption data indicates a UV maximum at exactly a 1:1 mole ratio of imidazole and Amlexanox. Although hydrogen bonding between imidazole and Amlexanox cannot be ruled out, the data suggest that charge interaction may occur in 95% ethanol. Thus, by neutralizing the negative charge on Amlexanox with imidazole, the hydrophobic portions of Amlexanox may partition into the ethanol phase to a greater extent. The same mechanism may be used for solubilizing other not very soluble drugs in a formulation.

EXAMPLE 3

Three ethanol-based gel formulations were prepared (Gel D, Gel E, and Gel F) using the following components (by weight): 95% ethanol, ethyl cellulose N-100 4%, ethyl cellulose N-50 4%, hydroxypropyl cellulose HF 1%, imidazole, polyvinylpyrrolidone K-90 8%, and Amlexanox. The ethanol, imidazole, and Amlexanox content in the formulations were as follows: 81.1%, 1.36%, and 0.5%, respectively for Gel D; 80%, 1.32%, and 2.5%, respectively for Gel E; and 76.7%, 1.28%, and 5%, respectively for Gel F. For Gels D-F, the final imidazole concentration in 95% ethanol was 200 mM. The final Amlexanox concentrations were varied in Gels D–F to make either a gel solution or a gel suspension of Amlexanox.

Gel D was a clear and viscous gel with all Amlexanox dissolved to a final concentration of 0.5% w/w. This final concentration of Amlexanox in the final formulation is very similar to the concentration of Amlexanox in 95% ethanol with 200 mM imidazole as shown in Example 2. In contrast, Gel E was a viscous gel with a slight whitish color and Gel F was a very viscous gel with a white color. For both Gel E and Gel F, Amlexanox was mostly suspended in the formulation.

In-vitro adhesive differences between Gels D-F were assessed using the protocol described in Example 1 except that the temperature of the water was held constant at 37±2° C. The dried Gels D-F remained intact and adhered to the glass cover slip for 1 hour and 45 minutes. Between 1 hour and 45 minutes and 2 hours and 10 minutes, all three dried films detached and remained intact in the stirring water for up to 4 hours at which time the study was stopped. Although there appeared to be no difference between Gels D–F containing different concentrations of Amlexanox, the films strongly adhered to negatively charged cover slips for an extended period of time at physiologic temperature.

EXAMPLE 4

Gel D from Example 3 was used to determine if the formulation was miscible with two different types of pharmaceutically acceptable propellant aerosols, propellant 152a and propellant A31. Propellant 152a is 1,1-difluoroethane and propellant A31 is iso-butane.

Gel D (4.27 g) was transferred to 120 ml clear coated aerosol vial (Wheaton; Product No. M937F). The vial was fitted with a 20 mm valve from Precision Valve (Ontario, Canada). The 20 mm valve components were as follows: actuator (0.406 mm MBU ext. tube, delta, white), stem (50.8×0.508 mm), stem gasket (Buna S90), spring (SS), housing (1.27 mm mid-capillary S90), ferrule (20 mm, 6.35 mm skirt, epoxy top/bottom), ferrule gasket (20 mm, Buna), and dip tube (1.524 mm I.D. mid-capillary).

The 20 mm valve was crimped to the vial containing the Gel D using a Model 3000-C Can Crimper (Aero-Tech Laboratory, Maryland, N.Y.). The vial with crimped 20 mm valve was weighed and then tared. Propellant 152a was added slowly using an adapter. After each small addition, the vial was mixed by light hand shaking and then weighed. After a total weight of 3.92 g of propellant 152a was added, no additional propellant was added. The final weight of the formulation in the vial was 8.18 g and consisted of 47.8% propellant 152a and 52.2% Gel D, by weight. The final formulation was a clear gel having greatly reduced viscosity by visual observation as compared to the original Gel D. It was concluded that Gel D and propellant 152a were miscible. The final formulation was sprayed onto a human volunteer's hand. The formulation aerosolized as a thick foamy spray and adhered to the skin. Once dry (about 2 minutes), the dried film adhered very strongly to the skin.

Gel D (4.54 g) was transferred to a different 120 ml clear coated aerosol vial and the vial was crimped with a 20 mm valve as described above. Propellant A31 was added as described above. After adding ~0.5 g of propellant A31, a thick weight precipitant formed that could not go into solution after hand shaking. It was concluded that propellant A31 was not miscible with Gel D formulation.

EXAMPLE 5

Two ethanol-based gel suspensions were prepared (Gel G, Gel H) using the following components (by weight): 95% ethanol, ethyl cellulose N-100 4%, ethyl cellulose N-50 4%, hydroxypropyl cellulose HF 0.25%, imidazole, polyvinylpyrrolidone K-90 8%, and Amlexanox. The ethanol, imidazole, and Amlexanox content in the formulations were as follows: 81.7%, 1.36%, and 0.5%, respectively for Gel G;

77.2%, and 1.3%, and 5%, respectively for Gel H. For Gel G and Gel H, the final imidazole concentration in 95% ethanol was 200 mM. The only difference between Gel G and Gel D formulations was the final concentration of hydroxypropyl cellulose (HPC). Gel D was more viscous since it had 1% HPC while Gel G had only 0.25% HPC. Gel F and Gel H, both made with a final concentration of 5% Amlexanox, also had the same difference in final concentration of HPC.

For Gels D, F, G, and H, approximately 4g of each formulation was transferred into four 120 ml vials. The vials with 20 mm valves were crimped and propellant 152a was added using the method described in Example 6. The amounts of each gel (with % Amlexanox and % HPC and propellant 152a added to make the final formulations) are summarized in Table 1 below.

these formulations was about 6.35 mm. As a result, it was more difficult to efficiently and completely cover a defined area on the absorbent pad.

In contrast, the spray pattern of less viscous formulations made with 0.5% HPC tended to be thinner and more efficiently and completely covered a wider area on the absorbent pad. Between samples D 1–D4 and G1–G4, there did not appear to be a significant difference between the spray pattern, except that it was noted that the 5% Amlexanox (samples F1–F4) formulations, in general, sprayed thicker than the 0.5% Amlexanox formulations (samples D1–D4). Thus, it was clear that the overall spray pattern was very much influenced by the viscosity of the overall formulation. Further, the spray pattern of formulations made with a greater percentage of propellant 152a were clearly more desirable.

TABLE 1

Compositions of Propellant Aerosol formulations of Amlexanox

| Sample No. | Amlexanox % (w/w) | HPC (% w/w) | Gel Weight (g) | Propellant 152a (g) | Total Formulation Weight (g) | Propellant 152a % (w/w) | Gel % (w/w) | Visual Observation of Final Formulation |
|---|---|---|---|---|---|---|---|---|
| D1 | 0.5 | 0.5 | 3.97 | 2.24 | 6.21 | 36.0% | 64.0% | clear sl. viscous solution |
| D2 | 0.5 | 0.5 | 4.01 | 3.35 | 7.36 | 45.5% | 54.5% | clear sl. viscous solution |
| D3 | 0.5 | 0.5 | 4.03 | 4.55 | 8.58 | 53.0% | 47.0% | clear sl. viscous solution |
| D4 | 0.5 | 0.5 | 4.00 | 3.90 | 7.90 | 49.3% | 50.7% | clear sl. viscous solution |
| F1 | 5.0 | 0.5 | 4.04 | 4.68 | 8.72 | 53.7% | 46.3% | white sl. viscous suspension |
| F2 | 5.0 | 0.5 | 4.02 | 2.30 | 6.32 | 36.4% | 63.6% | white sl. viscous suspension |
| F3 | 5.0 | 0.5 | 4.05 | 3.09 | 7.14 | 43.3% | 56.7% | white sl. viscous suspension |
| F4 | 5.0 | 0.5 | 4.04 | 3.86 | 7.90 | 48.9% | 51.1% | white sl. viscous suspension |
| G1 | 0.5 | 1.0 | 4.01 | 2.26 | 6.27 | 36.1% | 63.9% | clear viscous solution |
| G2 | 0.5 | 1.0 | 4.03 | 2.84 | 6.87 | 41.3% | 58.7% | clear viscous solution |
| G3 | 0.5 | 1.0 | 4.23 | 3.77 | 8.00 | 47.1% | 52.9% | clear viscous solution |
| G4 | 0.5 | 1.0 | 4.10 | 4.84 | 8.94 | 54.1% | 45.9% | clear viscous solution |
| H1 | 5.0 | 1.0 | 4.14 | 4.87 | 9.01 | 54.1% | 45.9% | white viscous suspension |
| H2 | 5.0 | 1.0 | 4.11 | 4.09 | 8.20 | 49.9% | 50.1% | white viscous suspension |
| H3 | 5.0 | 1.0 | 3.98 | 4.47 | 8.45 | 52.9% | 47.1% | white viscous suspension |
| H4 | 5.0 | 1.0 | 4.10 | 3.58 | 7.68 | 46.6% | 53.4% | white viscous suspension |

In all the above-listed formulations, the gels and propellant 152a were miscible to make final formulations that were either homogenous clear solutions or homogenous white suspensions. HPC concentrations of 1% in the gels led to final formulations that were more viscous as compared to gels that contained only 0.5% HPC.

Each of the final formulations listed above was sprayed onto an absorbent pad. The physical characteristics of the spray and spray pattern were recorded. In summary, final formulations made using 0.5% HPC (samples D1–D4 and F1–F4) provided for the most appropriate spray. Final formulations made using 1% HPC (samples G1–G4 and H1–H4) were quite viscous and tended to spray more like a mousse-or foam-type product. The width of the spray for

EXAMPLE 6

Quantification and stability of Amlexanox in Gel D (0.5% Amlexanox) and Gel F (5.0% Amlexanox) was determined using reverse phase HPLC with UV detection at 220 nm. A mobile phase of 57 mM Potassium Phosphate/NaOH Buffer (pH 8.0) and acetonitrile (650:350 volume ratio) was prepared and filtered through a 0.45 micron filter.

For the standard curve, exactly 50 mg Amlexanox was dissolved in 100 mL mobile phase and then serially diluted 1:2 to make ten standards in the range of 0 to 0.5 mg Amlexanox/niL. Exactly 1000 mg of Gel D and Gel F (in triplicate samples) was weighed into a tared 100 mL volumetric flask. Approximately 90 mL of mobile phase was added. After gentle hand mixing, the samples were allowed to sit overnight. The volumes in each volumetric flask were filled to the 100 mL mark with mobile phase, hand mixed, and filtered through a 0.45 micron filter.

For each sample containing Gel D, exactly 20 mL of the filtrate was added to a 50 mL volumetric flask and filled with mobile phase to the 50 mL mark. For each sample containing Gel F, exactly 2 mL of the filtrate was added to a 50 mL volumetric flask and filled with mobile phase to the 50 mL mark. The theoretical Amlexanox concentration in all samples was 0.02 mg/mL which was approximately the middle of the Amlexanox standard concentration curve. A placebo formulation sample made with no Amlexanox was also prepared using the same protocol as described above. All samples were assayed using a flow rate of 0.8 mL/min and an injection volume of 20 µL. The Amlexanox standard curve and tabulated results for the formulations are shown in the Table 2 and FIG. 3.

TABLE 2

Quantification of Amlexanox in Gel Solutions and Gel Suspensions containing Amlexanox

| Sample | HPLC AUC | Calc. [Amlex] mg/mL | [Amlex] (mg/mL) Avg. | Std. Dev. | % of Label | Storage at 25° C. (days) |
|---|---|---|---|---|---|---|
| PLACEBO | 3070 | 0.00000 | 0.0000 | 0.00000 | — | — |
|  | 3857 | 0.00000 |  |  |  |  |
|  | 4168 | 0.00000 |  |  |  |  |
| Gel D | 165336 | 0.01990 | 0.0198 | 0.00014 | 98.9% | 21 |
|  | 164619 | 0.01981 |  |  |  |  |
|  | 163077 | 0.01961 |  |  |  |  |
| Gel F | 178848 | 0.02158 | 0.0216 | 0.00001 | 107.9% | 21 |
|  | 178951 | 0.02160 |  |  |  |  |
|  | 178804 | 0.02158 |  |  |  |  |

Figure 3:
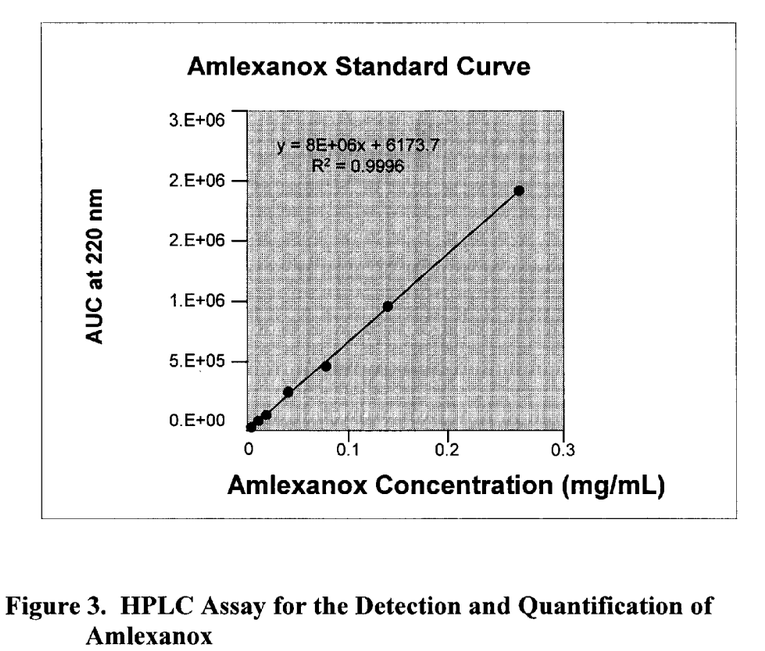
FIG. 3 is a graphical display of standard curve for a range of concentrations of Amlexanox in relation to its UV absorbance at 220 nm. This standard curve has been used to assay by HPLC methodology the Amlexanox formulations for their stability.

For the Amlexanox standard curve, the 0.5 mg/mL standard was omitted in the plot since it was clearly outside of the linear range of the assay. The HPLC data for Gel D and Gel F suggests that Amlexanox remains stable in both formulations since the actual Amlexanox concentration were nearly identical to or even greater than the Amlexanox concentration expected. No additional peaks for either formulation were detected that could not be explained by peaks also detected in the placebo samples.

EXAMPLE 7

Four ethanol-based gel formulations were prepared (Gel I, Gel J, Gel K, and Gel L) using the following components (by weight): 95% ethanol 82–84%, ethyl cellulose N-100 4%, ethyl cellulose N-50 4%, hydroxypropyl cellulose HF 0.5%, imidazole, polyvinylpyrrolidone K-90 8%, and Amlexanox 0.5%. The final imidazole concentration in the gels was 150 mM for Gel I, 100 mM for Gel J, 50 mM for Gel K, and 0 mM for Gel L. The final ethanol concentrations for each formulation were adjusted accordingly. The purpose of this experiment was to assess the role of imidazole concentration on the apparent solubility of Amlexanox in the gel formulations.

A visual observation of the gel formulations showed that there was a relationship between the final concentration of imidazole in the gels and the apparent solubility of Amlexanox. The color of Gel I with 150 mM imidazole was similar to that of Gel D with 200 mM imidazole, although Gel I was slightly opaque. Gel J and Gel K had a more whitish color indicating that Amlexanox was not completely dissolved. Further, Gel L was completely white, indicating that Amlexanox was mostly present undissolved and suspended in the gel. Thus, imidazole not only increases the solubility of Amlexanox in 95% ethanol, but also in the final formulation.

EXAMPLE 8

Two ethanol-based gel formulations were prepared (Gel M, Gel N) using the following components (by weight): 95% ethanol, ethyl cellulose N-100 2%, ethyl cellulose N-50 2%, hydroxypropyl cellulose HF 0.25%, imidazole, polyvinylpyrrolidone K-90 4%, and Amlexanox. The final ethanol, imidazole, and Amlexanox concentrations in the formulations were as follows: 89.7%, 1.5%, and 0.5%, respectively for Gel M; 85.3%, and 1.44%, and 5%, respectively for Gel N. The purpose of this experiment was to assess whether gel formulations (Amlexanox gel solution and gel suspension) with greatly reduced viscosity could be efficiently sprayed using propellant 152a.

Approximately 5 g of each formulation was transferred into four 120 mL Wheaton vials. The vials with 20 mm valves were crimped and propellant 152a was added using the method described in Example 4. Both gels were miscible with the propellant. To 5.04 g Gel M (0.5% Amlexanox) 2.03 g propellant 152a was added so that the final % propellant 152a was 28.7% w/w. To 5.08 g Gel N (5% Amlexanox) 2.15 g propellant 152a was added so that the final % propellant 152a was 29.7% w/w. The final formulations were sprayed on to a human volunteer's hand and into the mouth.

When sprayed onto the hand, both formulations sprayed evenly and efficiently and dried (within 2 minutes) to a robust film. When sprayed into the mouth, both formulations came in contact with the buccal region, spread, and dried into white films that remained adhered to the buccal surface for approximately 30 minutes. Thus, this experiment demonstrated that less viscous gel formulations could be efficiently aerosolized with a lower weight percentage of a pharmaceutically acceptable propellant and form films on both the skin and buccal surfaces.

EXAMPLE 9

Gel M (5.03 g) and Gel N (5.10 g) were transferred to 120 mL clear coated aerosol vial (Wheaton; Product no. M937F). The vials were fitted with a different 20 mm valve from Precision Valve (Ontario, Canada) that was intended to accommodate more viscous formulations. The new 20 mm valve components were as follows: actuator (1.219×2.083 mm NMBU delta, white), stem (50.8×0.508 mm), stem gasket (Buna S90), spring (SS), housing (2.032 mm Barbed S90), ferrule (20 mm, 6.35 mm skirt, epoxy top/bottom), ferrule gasket (20 mm, Buna), and dip tube (3.810 mm I.D. mid-capillary). The vials and 20 mm. valves were crimped and propellant 152a was added as described in Example 4.

The final weight of the formulation containing Gel M was 6.39 g and consisted of 21% propellant 152a. The final weight of the formulation containing Gel N was 6.77 g and consisted of 25% propellant 152a. The final formulation containing Gel M was clear and the final formulation containing Gel N was a homogenous white suspension. Each of the final formulations was sprayed onto a human volunteer's hand to evaluate both the quality of the spray as well as subsequent film formation. The spray from both formulations was suitable and a defined area of the skin was efficiently and completely covered. A smooth white film formed in each case within 2–3 minutes. The results to this experiment show that lower concentrations of propellant are needed to form a suitable spray and subsequent film when valves and dip tubes designed for more viscous formulations are used.

EXAMPLE 10

Approximately 5 mL Gel M (with 0.5% Amlexanox) was transferred into a 120 mL Wheaton vial. A pump-spray actuator designed to deliver a metered dose of 0.13 mL was attached. The P3 20 mm Snap-On assembly (Santos actuator 0.305 mm MBU insert with standard dip tube and 62–00040B1 Cap) was obtained from Precision Valve (Ontario, Canada). The actuator had to be pumped 5–6 times to fill the dip tube. Once the dip tube was completely filled, pressing down on the actuator resulted in the ejection of a thin stream of gel from small single orifice on the actuator. The thin stream of gel landed on a human volunteer's hand in a circle with a diameter of approximately 9.525 mm. The gel then spread to the approximate diameter of 12.7 mm and then dried to form a thick film within 8 minutes. An additional spray was pumped onto a different location of the hand and was immediately spread evenly with a finger to form a circle with an approximate diameter of 31.75 mm. Thus, this experiment demonstrated that a fixed volume of a gel formulation could be delivered using a pump spray actuator to the hand and result in the formation of a film.

EXAMPLE 11

One ethanol-based gel suspension was prepared (Gel O) using the following components (by weight): 95% ethanol 76.7%, ethyl cellulose N-100 6%, ethyl cellulose N-50 6%, Polycarbophil Noveon AA1 4%, 18% NaOH 2%, imidazole 0.32%, and Amlexanox 5%. The final imidazole concentration was 50 mM. Gel O was a white homogeneous stable suspension of Amlexanox Approximately 100 mg of the final formulation was placed on the gingival tissue in a human volunteer's mouth. A white film formed within seconds and hardened within 1 minute. The hardened film adhered very strongly to the gingiva and remained in place for approximately 45 minutes before dislodging intact.

EXAMPLE 12

One ethanol-based gel suspension was prepared (Gel P) using the following components (by weight): 95% ethanol 71.9%, ethyl cellulose N-100 8%, ethyl cellulose N-50 6%, Polycarbophil Noveon AA1 6%, 18% NaOH 3%, imidazole 0.31 1%, and Amlexanox 5%. Gel P was a white homogenous stable suspension of Amlexanox. Exactly 1.5 mL of Gel P was added to stirring 30 mL water (double-distilled). After 1.5 hours the pH was measured. The pH was 5.4.

EXAMPLE 13

Two ethanol-based gel suspensions were prepared (Gel Q, Gel R) using the following components (by weight): 95% ethanol, ethyl cellulose N-100 2%, ethyl cellulose N-50 2%, Polycarbophil Noveon AA1, 18% NaOH, imidazole 0.1%, Amlexanox 5%, water, and glycerin 1%. The final ethanol, Polycarbophil Noveon AA1, 18% NaOH, and water content were as follows: 63.9%, 8%, 4.5%, and 13.5% for Gel Q; and 65.4%, 6.5%, 3.7%, and 14.3% for Gel R. Gel Q and Gel R were white homogenous stable suspensions of Amlexanox. Exactly 2.0 mL of each gel was added to stirring 100 mL water (double-distilled). After 2.0 hours the pH was measured. The pH of Gel Q was 5.4 and the pH of Gel R was 5.5.

EXAMPLE 14

One ethanol-based gel suspension containing Amlexanox (Gel S) was prepared using the following components (by weight): 95% ethanol 63.9%, ethyl cellulose N-100 2%, ethyl cellulose N-50 2%, Polycarbophil Noveon AA1 8%, 18% NaOH 4.5%, imidazole 0.1%, Amlexanox 5%, water 13.5%, and glycerin 1%. One ethanol-based gel placebo (Gel T) was prepared using the following components: 95% ethanol 68.9%, ethyl cellulose N-100 2%, ethyl cellulose N-50 2%, Polycarbophil Noveon AA18%, 18% NaOH 4.5%, imidazole 0.1%, water 13.5%, and glycerin 1%. Gel S was a white homogenous stable suspension of Amlexanox. Gel T was also white in color but contained no Amlexanox. Exactly 0.5 g of each gel was added in to 25 mL water (double-distilled). After two hours the pH was measured. The pH of Gel S was 5.4 and the pH of Gel T was 5.3. The viscosity of Gel S was measured using a Brookfield Programmable Rheometer. The viscosity of Gel S was 708 cP.

Those skilled in the art will recognize that, while specific embodiments have been illustrated and described, various modifications and changes may be made without departing from the spirit and scope of the invention. Accordingly, the invention described herein should be understood in light of the entire disclosure, including the claims below, and that many equivalent embodiments are possible by applying the ordinary skill in the art of pharmaceutical sciences.

The above description is illustrative and not restrictive. Many variations of the invention will become apparent to those of skill in the art upon review of this disclosure. The scope of the invention should, therefore, be determined not with reference to the above description, but instead with reference to the appended claims along with their full scope of equivalents.

What is claimed is:

1. A non-water soluble, film-forming bioadhesive pharmaceutical gel comprising:
   a water-insoluble alkyl cellulose from about 0.1% to about 20% by weight of the gel;
   a solvent system comprising a mixture of from about 30% to about 90% by weight of at least one volatile solvent and from about 10% to about 25% by weight of water;
   a solubilization agent or a dispersing agent or a mixture thereof, wherein said solubilization agent or said dispersing agent is not polyactylic acid; and
   a pharmaceutical.

2. The gel of claim 1, wherein said alkyl cellulose is methyl cellulose, ethyl cellulose, propyl cellulose, or butyl cellulose, or a mixture thereof and wherein said volatile solvent is a lower alkyl alcohol, 1-methyl-2-pyrrolidone, a volatile silicone, a propellant, or a mixture thereof.

3. The gel of claim 1, wherein the solubilization agent is imidazole.

4. The gel of claim 1, wherein the pharmaceutical is not very soluble in the formulation in the absence of a solubilization agent.

5. The gel of claim 1, wherein the pharmaceutical is an analgesic, an anti-inflammatory agent, an antihistamine, an antipruritic, an anesthetic, a vasoconstrictor, an antihypertensive, a cardiac agent, a hemostatic, a styptic, a mucolytic, an antitussive, an expectorant, a mucoprotectant, an antineoplastic, an immunologic agent, an antibiotic, an antiviral, an antidiabetic, a bronchodilator, a sympathomimetic, an adrenergic blocker, an anticholinergic, an antimuscarinic, an antispasmodic, a skeletal muscle relaxant, a uterine drug, an antimigraine drug, a sedative, a hypnotic, an anxiolytic, a central nervous system stimulant, an antidepressant, an antiepileptic, an antiemetic, a hormone, a topical antifungal, a topical bactericide, a disinfectant, a protective and adsorbent, a demulcent, an emollient, an astringent, an antiperspirant, an irritant, a rubifacient, a vesicant, a keratolytic, a cauterizing agent, a cleansing agent, an antiphlogistic, an antipruritic, a sunscreen, a melanizer, a skin bleach, a depilatory agent, a hair growth enhancer, a vulnerary agent or an epithelizing agent, or a mixture thereof.

6. The gel of claim 1, further comprising from about 1% to about 10% by weight of a polymer having bioadhesive properties, wherein said bioadhesive polymer is polycarbophil, polyvinylprrolidone, sodium carboxymethyl cellulose, or a mixture thereof.

7. The gel of claim 6, wherein:
   said alkyl cellulose is ethylcellulose which constitutes from about 2% to about 20% by weight of the gel;
   said volatile solvent is ethanol which constitutes from about 50% to about 90% by weight of the gel;
   said polymer having bioadhesive properties is polyvinylpyrrolidone or polycarbophil;
   said solubilizing agent is imidazole which constitutes from about 0.01% to about 5% by weight of the gel;
   and said pharmaceutical is 2-aminio-7-(1-methylethyl)-5-oxo-5H-benzopyrano-pyridine-3-carboxylic acid, which constitutes from about 0.5% to about 5% by weight of the gel.

8. The gel of claim 1, further comprising a bioerodable polymer, wherein the bioerodable polymer is hydroxypropyl cellulose or a copolymer of lactic and glycolic acids, polycaprolactone, a polyorthoester, polyphosphazene or a mixture thereof, wherein the combination of said bioerodable polymer and said water-insoluble alkyl cellulose comprises from about 2% to about 25% by weight of the gel.

9. The gel of claim 1, further comprising an adjuvant.

10. The gel of claim 1, wherein the pharmaceutical is released in a controlled manner.

11. The gel of claim 1, wherein the pH of the formulation is from about 4.0 to about 7.0.

12. The gel of claim 11, wherein the propellant is 1,1-difluoroethane.

13. A non-water soluble, film-forming bioadheive pharmaceutical gel comprising:
   ethylcellulose which constitutes from about 01% to about 20% by weight of the gel;
   a solvent system comprising a mixture of at least one volatile solvent and from about 10% to about 25% by weight of water;
   a solubilization agent or a dispersing agent or a mixture thereof, wherein said solubilization agent or said dispersing agent is not polyacrylic acid; and
   a pharmaceutical.

14. The gel of claim 13, wherein said volatile solvent comprises a lower alkyl alcohol, 1-methyl-2-pyrrolidone, a volatile silicone, or a mixture thereof.

15. The gel of claim 13, wherein the volatile solvent comprises ethanol.

16. The gel of claim 14, wherein the gel is an aerosol formulation.

17. The gel of claim 14, further comprising a liquified gas propellant or a compressed gas propellant or a mixture thereof.

18. The gel of claim 17, wherein the propellant is 1,1-difluoroethane.

19. The gel of claim 13, wherein the pharmaceutical is an analgesic, an anti-inflammatory agent, an antihistamine, an antipruritic, an anesthetic, a vasoconstrictor, an antihypertensive, a cardiac agent, a hemostatic, a styptic, a mucolytic, an antitussive, an expectorant, a mucoprotectant, an antineoplastic, an immunologic agent, an antibiotic, an antiviral, an antidiabetic, a bronchodilator, a sympathomimetic, an adrenergic blocker, an anticholinergic, an antimuscarinic, an antispasmodic, a skeletal muscle relaxant, a uterine drug, an antimigraine drug, a sedative, a hypnotic, an anxiolytic, a central nervous system stimulant, an antidepressant, an antiepileptic, an antiemetic, a hormone, a topical antifungal, a topical bactericide, a disinfectant, a protective and adsorbent, a demulcent, an emollient, an astringent, an antiperspirant, an irritant, a rubifacient, a vesicant, a keratolytic, a cauterizing agent, a cleansing agent, an antiphlogistic, an antipruritic, a sunscreen, a melanizer, a skin bleach, a depilatory agent, a hair growth enhancer, a vulnerary agent or an epithelizing agent, or a mixture thereof.

20. The gel of claim 13, wherein the pharmaceutical is 2-amino-7-(1-methylethyl)-5-oxo-5H-[1]benzopyrano-[2,3-b]-pyridine-3-carboxylic acid, which constitutes from about 0.5% to about 5% by weight of the gel.

21. The gel of claim 13, further comprising imidazole which constitutes from about 0.01% to about 5% by weight of the gel.

22. The gel of claim 13, further comprising a bioerodable polymer, wherein the bioerodable polymer is hydroxypropylcellulose or a copolymer of lactic and glycolic acids, polycaprolactone, a polyorthoester, polyphosphazene, or a mixture thereof.

23. The gel of claim 13, further comprising an adjuvant.

24. The gel of claim 13, wherein the pharmaceutical is released in a controlled manner.

25. The gel of claim 13, wherein the pH of the formulation is from about 4.0 to about 7.0.

26. A non-water soluble, film-forming bioadhesive pharmaceutical gel comprising:
   ethylcellulose which constitutes from about 0.1% to about 20% by weight of the gel;
   ethanol which constitutes from about 60% to about 90% by weight of the gel;
   water up to about 25% by weight of the gel;
   hydroxypropylcellulose as a bioerodable polymer constituting up to about 2% by weight of the gel;
   polyvinylpyrrolidone, polycarbophil or a mixture thereof as a bioadhesive polymer constituting from about 1% to about 10% by weight of the gel;
   imidazole constituting from about 0.01% to about 5% by weight of the gel; and
   2-amino-7-(1-methylethyl)-5-oxo-5H-[1]benzopyrano-[2,3-b]-pyridine-3-carboxylic acid, which constitutes from about 0.5% to about 5% by weight of the gel.

27. The gel of claim 26, further comprising 1,1-difluoroethane as a propellant which constitutes from about 35% to 60% by weight of the gel.

28. A method for delivery of an effective amount of one or more pharmaceuticals to a skin surface or a mucosal surface comprising administering the gel of claim 1 to the skin surface or to the mucosal surface.

29. A method for delivery of an effective amount of one or more pharmaceuticals to a skin surface or a mucosal surface comprising administering the gel of claim 13 to the skin surface or to the mucosal surface.

30. The gel of claim 1, wherein the gel is an aerosol formulation.

31. The gel of claim 1, wherein said dispersing agent is a sorbitan ester, a gum, or a colloid.

32. The gel of claim 31, wherein said sorbitan ester is monooleate, monolaurate, monopalmitate, monostearate, trioleate, tristearate, polysorbate 20, polysorbate 40, polysorbate 60, or polysorbate 80.

33. The gel of claim 31, wherein said gum is acacia, tragacanth, xanthan, guar, or veegum.

34. The gel of claim 31, wherein said colloid is carrageenan, an alginate, gelatin, agar, or bentonite.

35. The gel of claim 1, wherein said dispersing agent is a copolymer or derivative of polyvinylpyrrolidone, polyvinyl alcohol, cellulose, polyethylene glycol, polyoxyethylene, poloxamers, or chitosan.

36. The gel of claim 1 wherein said dispersing agent is sodium lauryl sulfate, oleic acid and its salts and esters, N-acetyl-N-ethyl morpholinum ethosulfate, or glycerol monostearate.

37. The gel of claim 13, wherein said dispersing agent is a sorbitan ester, a gum, or a colloid.

38. The gel of claim 37, wherein said sorbitan ester is monooleate, monolaurate, monopalmitate, monostearate, trioleate, tristearate, polysorbate 20, polysorbate 40, polysorbate 60, or polysorbate 80.

39. The gel of claim 37, wherein said gum is acacia, tragacanth, xanthan, guar, or veegum.

40. The gel of claim 37, wherein said colloid is carrageenan, an alginate, gelatin, agar, or bentonite.

41. The gel of claim 13, wherein said dispersing agent is a copolymer or derivative of polyvinylpyrrolidone, polyvinyl alcohol, cellulose, polyethylene glycol, polyoxyethylene, poloxamers, or chitosan.

42. The gel of claim 13, wherein said dispersing agent is sodium lauryl sulfate, oleic acid and its salts and esters, N-acetyl-N-ethyl morpholinum ethosulfate, or glycerol monostearate.

43. The gel of claim 7, further comprising a liquefied gas propellant or a compressed gas propellant or a mixture thereof constituting from about 20% to about 60% by weight of the gel.

* * * * *